(12) United States Patent
Sonne (10) Patent No.: US 6,193,985 B1
(45) Date of Patent: *Feb. 27, 2001

(54) TOCOPHEROL COMPOSITIONS FOR DELIVERY OF BIOLOGICALLY ACTIVE AGENTS

(75) Inventor: Mette Rydahl Sonne, Brøndby Strand (DK)

(73) Assignee: A/S Dumex (Dumex Ltd), Copenhagen (DK)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/856,054

(22) Filed: May 14, 1997

Related U.S. Application Data (63) Continuation of application No. 08/441,759, filed on May 16, 1995, now abandoned.

(30) Foreign Application Priority Data

May 16, 1994 (GB) .................................................. 9409778

(51) Int. Cl.$^7$ .............................. A61K 9/00; A61K 9/107
(52) U.S. Cl. ......................... 424/400; 424/439; 424/484; 424/486; 514/772
(58) Field of Search ................................... 424/439, 450, 424/485, 486, 400, 484; 514/772

(56) References Cited

U.S. PATENT DOCUMENTS

| | | |
|---|---|---|
| 4,439,432 | 3/1984 | Peat . |
| 4,628,052 | * 12/1986 | Peat ........................................ 514/171 |
| 4,847,072 | * 7/1989 | Bissett et al. ........................... 424/59 |
| 4,863,720 | 9/1989 | Burghart et al. . |
| 4,950,664 | 8/1990 | Goldberg . |
| 4,960,814 | 10/1990 | Wu et al. . |
| 5,179,122 | * 1/1993 | Greene et al. ......................... 514/458 |
| 5,364,631 | * 11/1994 | Janoff et al. .......................... 424/450 |
| 5,430,021 | * 7/1995 | Rudnic et al. .......................... 514/14 |

FOREIGN PATENT DOCUMENTS

| | | |
|---|---|---|
| 24213/88 | 3/1989 | (AU) . |
| 70937/91 | 8/1991 | (AU) . |
| 3405240 | 8/1985 | (DE) . |
| 0 001 851 A1 | 5/1979 | (EP) . |
| 0387647 | 9/1990 | (EP) . |
| 0514967 | 11/1992 | (EP) . |
| 0539215 | 4/1993 | (EP) . |
| 0572190 | 12/1993 | (EP) . |
| 0636618 | 2/1995 | (EP) . |
| WO 86/04233 | 7/1986 | (WO) . |
| WO 89/03689 | 5/1989 | (WO) . |
| WO 91/14463 | 10/1991 | (WO) . |
| WO 91/16929 | 11/1991 | (WO) . |
| WO 93/03720 | 3/1993 | (WO) . |
| WO 93/18752 | 9/1993 | (WO) . |
| WO 93/21905 | 11/1993 | (WO) . |
| WO 94/20143 | 9/1994 | (WO) . |
| WO 95/01785 | 1/1995 | (WO) . |
| WO 95/11039 | 4/1995 | (WO) . |
| WO 95/24892 | 9/1995 | (WO) . |
| WO 95/30420 | 11/1995 | (WO) . |

OTHER PUBLICATIONS

Sokol et al.; "Improvement of cyclosporin absorption in children after liver transplantation by means of water–soluble vitamin E"; *The Lancet*; vol. 338: Jul. 27, 1991; pp.212–215.

Lau et al.; "Absorption of diazepam and lorazepam following intranasal administration"; *International Journal of Pharmaceutics*; 54 (1989) pp. 171–174.

Ismailos et al.; "Enhancement of cyclosporin A solubility by d–alphatocopheryl–polyethylene–glycol–1000 succinate (TPGS)"; *European Journal of Pharmaceutical Sciences*, 1 pp. 269–271(May 1994).

\* cited by examiner

Primary Examiner—Jeffrey C. Mullis
(74) Attorney, Agent, or Firm—Watov & Kipnes, P.C.; Allen R. Kipnes (57) ABSTRACT

The present invention provides the use of a tocopherol or a derivative thereof as a solvent and/or emulsifier for substantially insoluble and sparingly soluble biologically active agents, especially in the manufacture of pharmaceutical compositions. Such compositions are particularly suitable for transmucosal, and especially intranasal or rectal administration, or administration via the oral cavity.

30 Claims, 2 Drawing Sheets

TOCOPHEROL COMPOSITIONS FOR DELIVERY OF BIOLOGICALLY ACTIVE AGENTS

This is a continuation application of U.S. Ser. No. 08/441,759 filed on May 16, 1995 now abandoned.

The present invention is directed to new pharmaceutical compositions for delivery of biologically active agents. More particularly, the invention concerns the use of a tocopherol or a derivative thereof to prepare compositions having low irritability suitable for administration to mucosal membranes and which may be used efficiently to administer drugs, which are substantially insoluble or only sparingly soluble in water.

For systemic action, drugs are normally administered by mouth and are then absorbed in the gastrointestinal tract. However, this mode of administration is not suitable in all circumstances, for example in the case of drugs which are metabolised to any significant degree by the liver or which are poorly absorbed. In other cases, the oral route may be impractical, for example in patients suffering from nausea or who are unconscious. Before surgery, oral administration is not advisable because of the risk of vomiting and in many cases, a more rapid effect may be required than can be achieved by the oral route.

In these circumstances the parenteral route is frequently used, most notably intravenous or intramuscular injection. However, whilst this provides a convenient way of achieving a strong and rapid systemic effect, it has a number of disadvantages including the requirement for sterile equipment and trained personnel. It is also unpleasant to the patient.

Moreover, in cases where a systemic effect is not required, local administration may be preferable, for example to avoid side effects, to reduce the dosage, or simply to facilitate the administration.

Such problems have lead in recent years to an increasing interest in developing formulations for the topical administration of drugs, and in particular for topical administration involving absorption from mucous membranes.

Topical administration has the advantage that drugs may be administered readily and simply to achieve a systemic or dermal, regional or localised effect, as required. However, topical absorption of drugs through the skin can be slow, and in many cases transmucosal routes of delivery are preferred. Since it may be performed by untrained personnel and permits therapeutic plasma levels of drugs rapidly to be achieved, intranasal administration has received particular attention in this regard.

For topical delivery, biologically active drugs are normally administered in the form of aqueous solutions. However, many biologically active compounds are substantially insoluble or only sparingly soluble in water and in such cases, organic solvents are required to dissolve these agents. The problem here is that mucosal tissues are generally very sensitive and such solvents are frequently too irritant to be of clinical use. Thus for example, Lau and Slattery [Int. J. Pharm. 1989, p. 171–74] attempted to administer the benzodiazepines diazepam and lorazepam by dissolving these compounds in a range of solvents including: triacetin, DMSO, PEG 400, Cremophor EL, Lipal-9-LA, isopropyladipate and azone dodecyle-aza-cycloheptane-2-one. Whilst many of the solvents dissolved diazepam and lorazepam in the desired concentrations, when administered to the nose they were too irritant to be of use. Thus, Cremophor EL was found to be the least irritative for mucosal tissue, but nasal absorption using this solvent is rather slow and peak concentration is low relative to that found after iv. administration.

Triglycerides such as vegetable oils are generally non-irritant, but usually these oils are too poor as solvents to be of any use.

Attempts have been made to develop various other vehicles for transmucosal delivery of drugs, such as benzodiazepines, having limited water solubility. Thus, for example WO 86/04233 of Riker discloses a pharmaceutical composition wherein the drug (eg. diazepam) is dissolved in a mixture of propellant and co-solvent eg. glycerolphosphatide. The composition requires a pressurized system and at least one halogenated hydrocarbon aerosol propellant.

In U.S. Pat. No. 4,863,720 of Burghardt, a sublingual sprayable pharmaceutical preparation is disclosed, in which the active drug can be a benzodiazepine, optionally comprising polyethylene glycol (PEG) and requiring ethanol, di- and/or triglyceride of fatty acids and a pharmaceutically acceptable propellant gas.

U.S. Pat. No. 4,950,664 of Rugby-Darby describes the nasal administration of benzodiazepines in a pharmaceutically acceptable nasal carrier. The carrier may be a saline solution, an alcohol, a glycol, a glycol ether or mixtures thereof.

In PCT WO 91/16929 of Novo Nordisk, glycofurols or ethylene glycols are suggested as carriers for a variety of drugs, including benzodiazepines, which may be used on mucous membranes.

Another solution proposed to this problem, has been the use of micelles or liposomes, but these are frequently difficult to produce on a technical scale.

A further constraint concerning nasal administration is that a small administration volume is required; it is not generally possible to administer more than about 0.1 ml per dose per nostril. Therefore, a great need exists for solvents, in which, on the one hand the solubility of the active drug is high, and which, on the other hand, are non-irritating to the mucosa.

The aim of the present invention is to provide a solution to the above mentioned problems.

Tocopherols and their derivatives such as esters for example, are widely used in vitamin supplementation and as antioxidants in the food industry and in many pharmaceutical compositions. However, although in a few cases, a potential use in formulating pharmaceutical compositions has been reported, tocopherols and derivatives thereof have not generally previously been proposed as drug carriers.

Thus for example, European Patent Application No. 539,215 of Stafford-Miller suggests a possible use of Vitamin E and its derivatives as penetration enhancers in topical compositions.

WO 89/03689 of The Liposome Co., describes a liposome system based on acid derivatives of $\alpha$-tocopherol in a low pH aqueous medium for delivery of drugs which tolerate, or require, acid conditions.

The present invention is based on the surprising observation that tocopherols and derivatives thereof are excellent solvents for drugs which are substantially insoluble or sparingly soluble in water, whilst at the same time having a very low irritative potential for mucosal tissues.

As will be described in more detail below, it has also been found that certain tocopherol derivatives are efficient, non-irritant emulsifiers for such drugs, when dissolved in a tocopherol-based solvent.

In one aspect, the present invention thus provides the use of a tocopherol or a derivative thereof as a solvent and/or emulsifier for substantially insoluble and sparingly soluble biologically active agents, especially in the manufacture of pharmaceutical compositions.

A further aspect of the invention provides a composition for delivery of a substantially insoluble or sparingly soluble biologically active agent, comprising said agent dissolved in a tocopherol or a derivative thereof.

Tocopherols are a range of natural and synthetic compounds, also known by the generic term Vitamin E. α-Tocopherol (chemical name: 2,5,7,8-tetramethyl-2-(4',8', 12'-trimethyldecyl)-6-chromanole) is the most active and widely distributed in nature, and has been the most widely studied. Other members of the class include beta, gamma, and delta tocopherols but these are not used in pure form in therapeutics, although they are present in foodstuffs. Tocopherols occur in a number of isomeric forms, the D and DL forms being most widely available.

As used herein, the term "tocopherol" includes all such natural and synthetic tocopherol or Vitamin E compounds.

The melting point of natural α-tocopherol is between 2.5 and 3.5° C. α-Tocopherol is a viscous oil at room temperature, is soluble in most organic solvents, but insoluble in water.

Although tocopherols are available naturally in foodstuffs and may be extracted from plants, α-tocopherol is now mainly produced synthetically.

Any of the forms or isomers of tocopherols and their derivatives, eg. esters may be used according to the present invention. Thus for example, α-tocopherol can be used as such or in the form of its esters such as α-tocopherol acetate, linoleate, nicotinate or hemi succinate-ester, many of which are available commercially.

A special article of commerce is called Tenox GT-2 and consists of 70% tocopherol of natural origin, which has been concentrated from vegetable oil. This oil has a mild odour and a gentle taste.

The compositions of the present invention are particularly suited for application to mucous membranes in animals or humans, to deliver systemically substantially insoluble or sparingly soluble biologically active agents in a manner which ensures that a clinical effect is reached at least as rapidly as by conventional oral administration, with for instance tablets.

Thus, the compositions of the invention may be used for controlled release delivery of bioactive agents to achieve a beneficial or therapeutic effect over a prolonged period of time.

The compositions of the invention may also be applied to achieve a local effect, where desired, on the mucous membranes or the underlying tissue.

However, whilst the beneficial effects of the invention are particularly apparent in transmucosal delivery, the utility of the invention is not limited and compositions according to the invention may also be administered topically to all body surfaces, including the skin and all other epithelial or serosal surfaces, as well as parenterally or enterally, eg. as implants or by intravenous, intramuscular or subcutaneous injection, by infusion, or orally.

Transmucosal delivery is preferred however, and compositions according to the invention may be administered to mucosal membranes for example in the nose, vagina, rectum, ears, eyes, oral cavity, lungs, genito-urinary tracts, and gastro-intestinal tract. Nasal, rectal and oral cavity administrations are particularly preferred.

The compositions of the invention may be used directly as solutions of the bioactive agent in the tocopherol solvent. However such solutions are viscous, and the viscosity may be too high for certain applications, for example to achieve a sprayable formulation for nasal application.

Viscosity can be reduced by addition of co-solvents such as ethanol, but this is less desired, since solutions of this kind tend to be irritating to certain mucosal tissues.

Alternatively, the tocopherol solutions may be emulsified, to obtain formulations of lower viscosity. This may be achieved in known manner, by mixing the tocopherol-based "oil phase" containing the dissolved bioactive agent with an appropriate aqueous phase, eg. water, saline or buffer solutions.

Methods and appropriate aqueous media for obtaining emulsions are well known in the art and described in the literature. Emulsions according to the invention may be oil-in-water (O/W) or water-in-oil (W/O) emulsions. Generally speaking, O/W emulsions may be achieved when the oil phase contains up to about 70% lipids. W/O emulsions are formed when the oil phase exceeds c.a. 70%.

For nasal administration, due to the small administration volume required, it has generally been found that a high concentration of the oil (or lipid) phase is required. Emulsions with high lipid content are technically difficult to achieve and may be unstable. It may therefore be necessary to employ an emulsifier in order to form a stable emulsion. A wide range of emulsifiers are well known, both in the food and pharmaceutical arts, and are widely described in the literature. However, stability and viscosity may still be a problem, where very high contents of the oil phase are required. Moreover, some of the more widely available commercial emulsifiers, eg. phospholipids, polysorbates or various sorbitan esters of fatty acids may be irritating to the more sensitive mucosal tissues, such as those of the nose.

The inventors have surprisingly found however that tocopherol derivatives, particularly certain esters, may themselves form efficient, non-irritating emulsifiers to enable stable emulsions to be formed, even where high lipid levels are involved eg. about 50–70%. Particular mention may be made in this regard of Vitamin E TPGS which is a water soluble derivative of Vitamin E and consists of α-tocopherol, which is esterified with succinic acid, the other acidic group of the latter being esterified with polyethylene glycol 1000. Vitamin E TPGS is an almost odourless waxy amphiphilic substance with a molecular weight about 1513. The melting point is about 36° C. and its solubility in water is about 20%.

Stable emulsions may readily be achieved according to the invention using a range of tocopherols or derivative compounds as solvents, with Vitamin E TPGS as emulsifier, and any suitable aqueous medium.

A further aspect of the invention thus provides a composition suitable for delivery of substantially insoluble or sparingly soluble biologically active agents, comprising a tocopherol or a derivative thereof, and Vitamin E TPGS as emulsifier.

The tocopherol derivative emulsifier of the invention may be used alone or in conjunction with other known emulsifiers eg. phospholipids, polysorbates, sorbitan esters of fatty acids, cetearyl glucoside or poloxamers.

It has furthermore surprisingly been shown that various other solvents may be used in the emulsion system described above, without compromising the stability of the emulsion.

When the emulsion according to the present invention is of the oil-in-water type, it is desirable that the droplet size is as small as possible. It has been shown that by using systems according to the invention, for example, α-tocopherol, water, Vitamin E TPGS and bioactive agent, it is possible to form stable emulsions with an initial droplet size in the range 0.01–100 pm, preferably 0.01–50 μm, most preferably 0.1–20 μm.

The compositions which may be prepared according to the present invention, may contain any biologically active agent which is insoluble or sparingly soluble in water, ie.

with a solubility in water (w/v) which is 3% or less. For example such agents may include any bioactive agent which has less than 1% (w/v) solubility in water. Representative active agents from a range of different therapeutic groups are listed below, by way of exemplification.

Hormones and hormone-like substances of the steroid-group:

Corticosteroids such as cortisone, hydrocortisone, prednolone, prednisolone, triamcinolone acetonide, dexamethasone, flunisolide, budesonide, toxicorole pivalate, betametasone, beclomethasone dipropionate, fluticasone etc;

Sex-hormones such as: estradiol, progesterone, testosterone etc;

Antibiotics: Tetracyclines such as tetracycline, doxycycline, oxytetracycline, chloramphenicol etc; Macrolides such as erythromycin and derivatives, etc;

Antivirals: such as acyclovir, idoxuridine, tromantadine etc;

Antimycotics: Miconazole, ketoconazole, fluconazole, itraconazole, econazole, terconazole, griseofulvin, and polyenes such as amphotericin B or nystatine etc;

Anti-amoebics: Metronidazole, metronidazole benzoate and tinidazole etc;

Anti-inflammatory drugs: NSAID's such as indomethacin, ibuprofen, piroxicam, diclofenac etc;

Anti-allergics: Disodium cromoglycate etc;

Immunosuppressive agents: cyclosporins etc;

Coronary drugs: including vasodilators such as nitroglycerin, isosorbide dinitrate, Calcium-antagonists such as verapamile, nifedipine and diltiazem, Cardiac-glycosides such as digoxine.

Analgesics: eg. morphine, buprenorphine, etc;

Local anaesthetics: eg. lidocaine, etc;

Anxiolytics, sedatives & hypnotics: diazepam, nitrazepam, flurazepam, estazolam, flunitrazepam, triazolam, alprazolam, midazolam, temazepam, lormetazepam, brotizolam, clobazam, clonazepam, lorazepam, oxazepam, buspirone, etc;

Migraine relieving agents: sumatriptan, ergotamines and derivatives etc;

Drugs against motion sickness: eg. cinnarizine, anti-histamines, etc;

Anti-emetics: eg. ondansetron, tropisetron, granisetrone, metoclopramide, etc.

Others: such as disulfiram, vitamin K, etc.

The emulsions according to the present invention are especially suitable for nasal application because of their low index of irritability and are therefore particularly well suited to the delivery of biologically active drugs influencing the central nervous system (CNS).

Other biologically active agents which may be used include peptides, hormones, etc. The active substance may be present in an amount of from about 0.0001% to 50% of the total composition, preferably 0.001% to 40% (w/w).

Generally speaking compositions of the invention may contain from 1 to 99.99% (w/w), preferably 20 to 99.99%, most preferably 40 to 99.99% (w/w) of the tocopherol or tocopherol derivative solvent. The emulsion used in compositions of the invention may contain 1 to 95% (w/w) of the tocopherol or derivative thereof, preferably 20 to 95% (w/w), most preferably 35 to 80% (w/w).

As mentioned above, the emulsions of the present invention can be prepared by conventional means, by heating the oil and aqueous phases separately, and then mixing the two phases. The active ingredient can be dissolved in the lipid fraction of the tocopherol solvent and other solvents may be added if desired. The emulsifier, eg. Vitamin E TPGS, and optionally other emulsifiers, can be added to either the oil and/or the water phase. The water phase is then vigorously mixed with the oil phase. Mixing, eg. stirring may be continued as required eg. for up to 2 hours. Depending on the viscosity of the emulsion, a magnetic stirrer, a low shear mixer or the like can be used. If necessary, the emulsion can be processed by a low shear mixer and a high pressure homogenizer to achieve the desired droplet size. The formulations may be inspected microscopically to measure the droplet size and to be sure that no precipitation has taken place. The type of emulsion formed may be determined readily by a colour test using an oil- and/or water-soluble dye. To confirm the result, it may be examined whether the emulsion is easy to wash off with water or not. An O/W emulsion is coloured with the water-soluble dye and is very easy to wash off with water. A W/O emulsion is coloured with the oil-soluble dye and is very difficult to wash off with water.

In a further aspect, the present invention thus provides a method of preparing a composition for delivery of a substantially insoluble or sparingly soluble biologically active agent, said method comprising dissolving said agent in an amount of a tocopherol or a derivative thereof, sufficient to dissolve said agent.

In a preferred aspect, the method of the invention further comprises forming an emulsion of said tocopherol/biologically active agent solution, by mixing with an aqueous phase, optionally in the presence of an emulsifier, preferably vitamin E TPGS.

The compositions of the invention may take any of the conventional pharmaceutical forms known in the art, and may be formulated in conventional manner, optionally with one or more pharmaceutically acceptable carriers or excipients. Thus for example the compositions may take the form of ointments, creams, solutions, salves, emulsions, lotions, liniments, aerosols, sprays, drops, pessaries, suppositories, tablets, capsules or lozenges.

In a still further aspect, the present invention provides the use of a tocopherol or a derivative thereof for the preparation of a composition for delivery of a substantially insoluble or sparingly soluble biologically active agent to a human or non-human animal subject.

Alternatively viewed, the invention can be seen to provide a method of treatment of a human or non-human animal subject by delivery of a substantially insoluble or sparingly soluble biologically active agent, said method comprising administering to said subject a composition of the invention as hereinbefore defined.

The formulations according to the invention may be optimized with respect to bioadhesion, sprayability and viscosity, as desired. Thus for example, the following co-solvents may be added:

Vegetable oils such as sesame- or olive- or fractionated coconut oil, alcohols such as ethanol, propylene glycol, glycerol, polyethylene glycol or benzyl alcohol; or triacetin.

To optimize the stability of the emulsions, it may be appropriate to add surfactants such as Vitamin E TPGS poloxamers (eg. Pluronic®), cetearyl glucoside, polysorbates or sorbitan esters of fatty acids, or any of the other surfactants well known in the art, or other stabilisers such as xanthan gum, or propylene glycol alginate.

It is also possible to enhance the bioadhesive properties of the formulations according to the present invention by addition of bioadhesive polymers such as:

polyacrylic polymers such as carbomer and carbomer derivatives, eg. Polycarbophil or Carbopol etc;

cellulose derivatives such as hydroxymethyl-cellulose, hydroxyethylcellulose, hydroxypropyl-cellulose or sodium carboxymethylcellulose etc;

natural polymers like gelatin, sodium alginate, pectin etc; more generally, any physiologically acceptable polymer showing bioadhesive characteristics may be used.

To ensure that the formulations have a reasonable shelf-life it may be desirable to include preservatives such as benzalkonium chloride, sodium edetate, sorbic acid, potassium sorbate, phenoxyethanol, phenetanol, parabens or others known in the art. Addition of odour- or taste-masking compounds can also be desirable.

The invention will now be described in more detail in the following non-limiting Examples, with reference to the drawings in which:

EXAMPLES

As already mentioned, administration of drugs with very low water solubility to the nose is difficult, because of the limited volume which is acceptable for the nose (about 100 $\mu$l). The first example has a very high concentration of diazepam, and it is possible to administrate diazepam to the nose and to achieve a rapid clinical effect.

Example 1

A diazepam nosedrop preparation is made as follows: (100 g)

5 g of diazepam is mixed with 44 g of Tenox GT2, and 22 g of triacetin, and 5 g of Vitamin E TPGS. The oil phase is heated slowly to a homogeneous phase is achieved. To the water phase, 1.45 g of Pluronic F-68 (poloxamer 188) and 0.01 g of benzalkonium chloride are added, the water phase is heated slowly to a homogeneous phase is achieved. The water phase is vigorously mixed into the oil phase by using a magnetic stirrer. Thereafter, the emulsion is cooled to room temperature still on the magnetic stirrer. The emulsion was a pale yellow o/w emulsion, where the mean droplet size was about 1–2 $\mu$m.

This formulation (1) was tested in 8 rabbits in a randomized cross-over study compared with a commercially available diazepam formulation, Stesolido 5mg/ml for injection, (2).

Formulation 1 was given intranasally (i.n.) with a Eppendorf Multipette® 4780. Each rabbit was held in a supine position during and one minute after i.n. dosing in one nostril. The rabbits receive a volume that equals 2 mg diazepam, 40% of formulation 1. After each administration the actual dose received is estimated by visual inspection of the pipette tip and the rabbit nostrils. Only applications volumes estimated to 80% are accepted.

Formulation 2 was given as an ear-vein infusion during M minute. The rabbits received 0.4 ml Stesolid® 5 mg/ml (equals 2 mg diazepam). The rabbits were placed in a supine position for half a minute to attain the same experimental conditions as for i.n. dosing.

The rabbits were then tested with respect to pharmacodynamic response in the following way:

Hind legs to one side and the rabbit must stay in this position even after a firm tip with a finger on the hip.

The test is immediately repeated with both legs placed on the other side.

The rabbits were tested approximately once per minute until positive pharmacodynamic response, and thereafter tested every 2 minutes. Total test period is 20 minutes. The same person has dosed and tested all the rabbits in the present study.

The time to pharmacodynamic response is 4.4 minutes (mean, n=8) using formulation 1 and 1.6 minutes (mean, n=8) using formulation 2.

Example 2

A diazepam nosedrop preparation is made as follows: (100 g)

5 g of diazepam is mixed with 45.4 g of Tenox GT2, and 22.7 g of triacetin, and 15 g of Vitamin E TPGS. The oil phase is heated slowly to a homogeneous phase is achieved. To the water phase, 1.45 g of Pluronic F-68 (poloxamer 188) and 0.01 g of benzalkonium chloride are added, the water phase is heated slowly to a homogeneous phase is achieved. The water phase is vigorously mixed to the oil phase by using a magnetic stirrer. Thereafter, the emulsion is cooled to room temperature still on the magnetic stirrer. The emulsion is a clear orange w/o emulsion.

A less concentrated formulation of diazepam is required for the rectal administration, but still it can be very difficult to find an acceptable vehicle with low irritation.

Example 3

A diazepam enema preparation is made as follows: (100 g)

1 g of diazepam is mixed with 40 g of (-tocopherol, and 15 g of Vitamin E TPGS. The oil phase is heated slowly to a homogeneous phase is achieved. 5 g of ethanol is added to the oil phase immediately before mixing with the water phase. To the water phase, 2.5 g of Pluronic F-68 (poloxamer 188), and 0.01 g of benzalkonium chloride, and 0.05 g of disodium edetate are added, the water phase is heated slowly to a homogeneous phase is achieved. The water phase is vigorously mixed to the oil phase by using a magnetic stirrer. Thereafter, the emulsion is cooled to room temperature still on the magnetic stirrer. The emulsion is a white o/w emulsion.

Cinnarizine is used for motion sickness. Like diazepam, the drug has a very low water solubility. It will be a great advantage if the patient can administer the drug easily and have a rapid effect.

Example 4

A cinnarizine nosedrop formulation is made as follows: (100 g)

5 g of cinnarizine is mixed with 64 g of α-tocopherol, and 8 g of Vitamin E TPGS. The oil phase is heated slowly to a homogeneous phase is achieved. To the water phase, 1.5 g of Pluronic F-68 (poloxamer 188), and 0.01 g of benzalkonium chloride, and 0.05 g of disodium edetate are added, the water phase is heated slowly to a homogeneous phase is achieved. The water phase is vigorously mixed to the oil phase by using a magnetic stirrer. Thereafter, the emulsion is cooled to room temperature still on the magnetic stirrer. The emulsion is a white o/w emulsion.

Miconazole is used for the local treatment of infections caused by fungi. The next two formulations show formulations for use in the oral cavity and the vagina.

Example 5

A miconazole preparation for the oral cavity is made as follows: (100 g)

20 g of miconazole is mixed with 58.8 g of α-tocopherol, and 13 g of Vitamin E TPGS. The oil phase is heated slowly to a homogeneous phase is achieved. 5 g of ethanol is added to the oil phase immediately before mixing with the water phase. To the water phase, 1.5 g of Pluronic F-68 (poloxamer 188), and 0.01 g of benzalkonium chloride, and 0.05 g of disodium edetate are added, the water phase is heated slowly to a homogeneous phase is achieved. The water phase is added very slowly to the oil phase under vigorously mixing by using a magnetic stirrer. Thereafter, the emulsion is cooled to room temperature still on the magnetic stirrer. The emulsion is a yellow to brown w/o emulsion.

Example 6

A miconazole vaginal cream is made as follows: (100 g)

5 g of miconazole is mixed with 38 g of α-tocopherol, and 38 g of Vitamin E TPGS. The oil phase is heated slowly to a homogeneous phase is achieved. To the water phase, 2.5 g of Pluronic F-681 (poloxamer 188) and 0.01 g of benzalkonium chloride, and 0.05 g of disodium edetate are added, the water phase is heated slowly to a homogeneous phase is achieved. The water phase is vigorously mixed to the oil phase by using a low shear mixer. Thereafter, the emulsion is cooled to room temperature still mixed by the low shear mixer. The emulsion is a glossy, beige w/o emulsion. The emulsion has a consistency as an ointment and is very sticky.

The following Examples are divided into three subsections covering 1) Solubility; 2) Compositions and 3) Pharmacology/toxicology.

Example 7

Solubility

For the following, non-limiting, sparingly soluble drugs in water, the solubility in α-tocopherol and sesame oil are listed in Table 1:

Sesame oil was chosen as the reference, because it is a very commonly used and well tolerated vegetable oil. The solubilities in sesame oil and α-tocopherol were investigated by visual inspection of the saturation point.

TABLE 1

| Active agent | g drug in 100 g of α-tocopherol | g drug in 100 g of sesame oil |
| --- | --- | --- |
| Diazepam | 12 | 2 |
| Alprazolam | 4 <x< 6 | <0.2 |
| Midazolam | >13 | 1 <x< 2 |
| Cinnarizine | 11 <x< 18 | 2 <x< 4 |
| Metoclopramide | 2 <x< 4 | <2 |
| Budesonide | 1 <x< 2 | <0.1 |
| Miconazole | 60 | 5 <x< 10 |
| Metronidazole benzoate | 12 <x< 14 | <2 |
| Lidocaine | >45 | >18 |
| Disulfiram | 5 | 3 <x< 4 |
| Progesterone | >30 | 2 <x< 4 |
| Testosterone | 16 <x< 18 | 0.6 <x< 1 |

All the investigated biologically active agents show a surprisingly high solubility in α-tocopherol.

Compositions

In the following, non-limiting Examples, several drugs are shown in a number of different types of administration forms.

The emulsions were prepared as follows:

The oil and the water phase were heated slowly until homogeneous phases were achieved.

The warm water phase was vigorously mixed into the oil phase. Then, the emulsion was slowly cooled to room temperature while stirring. The emulsion may be homogenized.

The preparation of the solutions was made as simple solution, in which the preparations were stirred until the drug was completely dissolved.

As already mentioned, administration of drugs with low water solubility to the nose is very difficult, because of the limited acceptable volume for the nose (about 100 μl). The following examples have very high concentration of diazepam, so it was possible to administer diazepam to the nose and to get a fast clinical effect.

Example 8

An O/W emulsion of diazepam as a nosedrop (100 g):

| Oil phase: | Diazepam | 5.000 g |
| --- | --- | --- |
| | α-Tocopherol | 59.000 g |
| | Vitamin E TPGS. | 5.000 g |
| Water phase: | Disodium edetate | 0.050 g |
| | Potassium sorbate | 0.200 g |
| | Xanthan gum | 0.025 g |
| | purified water to | 100.000 g |

The water phase was adjusted to pH 4.7 by 1N HCl.

Example 9

An O/W emulsion of diazepam as nosedrop (100 g):

| Oil phase: | Diazepam | 5.000 g |
| --- | --- | --- |
| | α-Tocopherol | 58.000 g |
| | Sorbitan trioleate | 0.500 g |
| | Fractionated coconut oil | 5.000 g |
| Water phase: | Potassium sorbate | 0.200 g |
| | Poloxamer 188 | 1.000 g |
| | Xanthan gum | 0.030 g |
| | Polysorbate 80 | 0.500 g |
| | Purified water to | 100.000 g. |

The water phase was adjusted to pH 4.5 by 2N HCl.

Example 10

An O/W emulsion of diazepam as nosedrop (100 g):

| Oil phase: | Diazepam | 5.000 g |
| --- | --- | --- |
| | α-Tocopherol | 50.000 g |
| | Triacetin | 10.000 g |
| | Cetearyl glucoside | 2.000 g |
| | Methylparahydroxybenzoate (MPHB) | 0.080 g |
| | Propylparahydroxybenzoate (MPHB) | 0.040 g |
| Water phase: | Poloxamer 188 | 3.000 g |
| | Xanthan gum | 0.030 g |
| | Purified water to | 100.000 g. |

Example 11

A solution of diazepam, eg. as nosedrop, (25 g):

| | |
|---|---|
| Diazepam | 1.250 g |
| α-Tocopherol | 10.000 g |
| Triacetin | 13.750 g |

A less concentrated formulation of diazepam is needed for the rectal administration, but still it can be very difficult to find an acceptable vehicle with low irritation.

Example 12

A solution of cinnarizine, eg. as drops for administration to the oral cavity (25 g):

| | |
|---|---|
| Cinnarizine | 1.250 g |
| α-tocopherol | 17.500 g |
| ethanol | 1.250 g |
| fractionated coconut oil | 5.00 g |

A study has shown, that cinnarizine has a higher oral bioavailability, if it is dissolved in a vehicle before administration, [J. Pharm. Sci., vol 76, no. 4, p. 286–288, 1987], an example of such a vehicle could be α-tocopherol.

Example 13

A solution of cinnarizine, eg. for oral administration in capsules, (25 g):

| | |
|---|---|
| Cinnarizine | 0.750 g |
| α-Tocopherol | 24.250 g |

Miconazole is used locally for treatment of infections caused by fungi. The following examples show formulations for the oral cavity and the vagina.

Example 14

A solution of miconazole e. g. as drops for administration to the oral cavity (25 g).

| | |
|---|---|
| Miconazole | 6.250 g |
| α-Tocopherol | 16.875 g |
| Ethanol | 1.875 g |

Budesonide is a very potential drug, and is used as a local corticoid, e. g. for rhinitis.

Example 15

An O/W emulsion of budesonide as nosedrop or nasal spray (50 g).

| | | |
|---|---|---|
| Oily phase: | Budesonide | 0.025 g |
| | α-tocopherol | 12.500 g |
| | Vitamin E TPGS | 5.000 g |
| Water phase: | Potassium sorbate | 0.100 g |
| | Xanthan gum | 0.020 g |
| | Purified water to | 100.000 g |

The water phase is adjusted to pH 4.5 with 2N HCl.

Example 16

A solution of budesonide as nosedrop (25 g).

| | |
|---|---|
| Budesonide | 0.025 g |
| α-tocopherol | 10.000 g |
| Sesame oil | 14.975 g |

Alprazolam is a benzodiazepine which is used for the treatment of e. g. anxiety, therefore a rapid effect is desired in a easy way.

Example 17

An o/w emulsion of alprazolam as nosedrop or nasal spray (100 g).

| | | |
|---|---|---|
| Oily phase: | Alprazolam | 0.500 g |
| | α-tocopherol | 20.000 g |
| | Vitamin E TPGS | 10.00 g |
| Water phase: | Potassium sorbate | 0.200 g |
| | Xanthan gum | 0.050 g |
| | Purified water to | 100.000 g |

The water phase is adjusted to pH 4.5 with 2N HCl.

Example 18

A solution of alprazolam, e.g. as drops for administration in the oral cavity (25 g).

| | |
|---|---|
| alprazolam | 0.125 g |
| α-tocopherol | 13.750 g |
| sesame oil | 11.125 g |

Midazolam is a benzodiazepine tranquiliser with a sedative effect e.g., and is used for the treatment of anxiety and tension states, and as a sedative and for premedication. Midazolam has a very high first-pass effect after oral administration.

Example 19

An O/W emulsion of midazolam as nosedrop (50 g).

| | | |
|---|---|---|
| Oily phase: | Midazolam | 1.250 g |
| | α-Todopherol | 29.500 g |
| | Vitamin E TPGS | 2.500 g |
| Water phase: | Potassium sorbate | 0.100 g |
| | Xanthan gum | 0.013 g |
| | Poloxamer 188 | 0.750 g |
| | Disodium edetate | 0.025 g |
| | Purified water to | 100.000 g |

The water phase is adjusted to pH 4.5 with 2N HCl.
Disulfiram is used in the treatment of chronic alcoholism.

Example 20

A solution of disulfiram, e. g. as an oral solution or for oral administration by capsules (25 g).

| | |
|---|---|
| Disulfiram | 1.125 g |
| α-Tocopherol | 23.875 g |

Example 21

An O/W emulsion of lidocaine for treatment of e.g. insect bites (100 g).

| | | |
|---|---|---|
| Oily phase: | Lidocaine | 5.000 g |
| | α-Tocopherol | 40.000 g |
| | Cetearyl glucoside | 4.000 g |
| | MPHB | 0.080 g |
| | PPHB | 0.040 g |
| Water phase: | Poloxamer 188 | 3.000 g |
| | Xanthan gum | 0.030 g |
| | Purified water to | 100.000 g |

Example 22

Pharmacology

Studies on Rabbits

Preparations containing CNS active and muscle relaxing drugs such as diazepam and midazolam were tested in a pharmacodynamic model in rabbits.

The model consists of the following tests:

Test 1:
Hind legs to one side and the rabbit must stay in this position even after a firm tip with a finger on the hip. The test is immediately repeated with both legs placed on the other side.

Test 2:
Hind legs stretched out backwards and the rabbit must stay in this position even after a firm tip with a finger on the hip.

Test 3:
The rabbit must stay in a supine position, when placed in such a position.

After administration of the formulations (i.n., oral or i.v.) the rabbits were exposed to the three tests approximately once per minute until positive pharmacodynamic response, and thereafter every 2 minutes. The total test period was 20 minutes after i.n. and i.v. administration and 30 minutes after peroral administration.

The time elapsed from administration until the first positive response in test 1 was used to compare the onset of action of the different formulations.

Study 1

This pharmacodynamic study compared the nasal formulation of Example 8 (C) containing 5% of diazepam to a commercially available diazepam formulation, Stesolido 2mg tablet, Dumex (D). The study was run in 8 rabbits in a randomized cross-over study. The rabbits were tested for pharmacodynamic response as described previously, but the test period was 30 minutes after peroral administration to be sure to obtain a pharmacodynamic effect.

Formulation C was given intranasally (i.n.) with a laboratory pipette. Each rabbit was held in a supine position during and one minute after i.n. dosing in one nostril. The rabbits received a volume equivalent to 2.5 mg diazepam. After each administration the actual dose received is calculated by subtraction of the weight of the pipette before and after administration. Only applications determined to 80% (2 mg diazepam) were accepted.

Formulation D was given as an oral administration using a stomach pump. The tablet was dissolved in 5 ml water immediately before administration. The tube was rinsed with 10 ml water.

The time to onset of pharmacodynamic response in test 1 is 4.5 minutes (median, n=7) using formulation C and 19.4 minutes (median, n=8) using formulation D.

Study 2

This pharmacokinetic study compared the nasal formulation of Example 8 (C) containing 5% of diazepam to a commercially available diazepam formulation, Stesolido 2mg tablet, Dumex (D). The study was run in 8 rabbits in a randomized cross-over study.

Formulation C was given intranasally (i.n.) as described in study 1.

Formulation D was given by oral administration as described in study 1 using a stomach pump.

Blood samples from the ear-vein were taken before administration (time=0) and at 2, 5, 10, 15, 30, 45, 60, 75, 90, 120, 180 and 240 minutes.

Serum was analyzed for diazepam and the metabolite, desmethyldiazepam using Gas Chromatografy (GC). The limit of detection was 5ng/ml for both substances.

The pharmacokinetic parameters found for diazepam were $t_{max}$=23 minutes (median, n=6), $C_{max}$=68.2 ng/ml (median, n=6) after administration of formulation C and $t_{max}$=45 minutes (median, n=6), $C_{max}$=9.7 ng/ml (median, n=6) after administration of formulation D.

Figure 1:
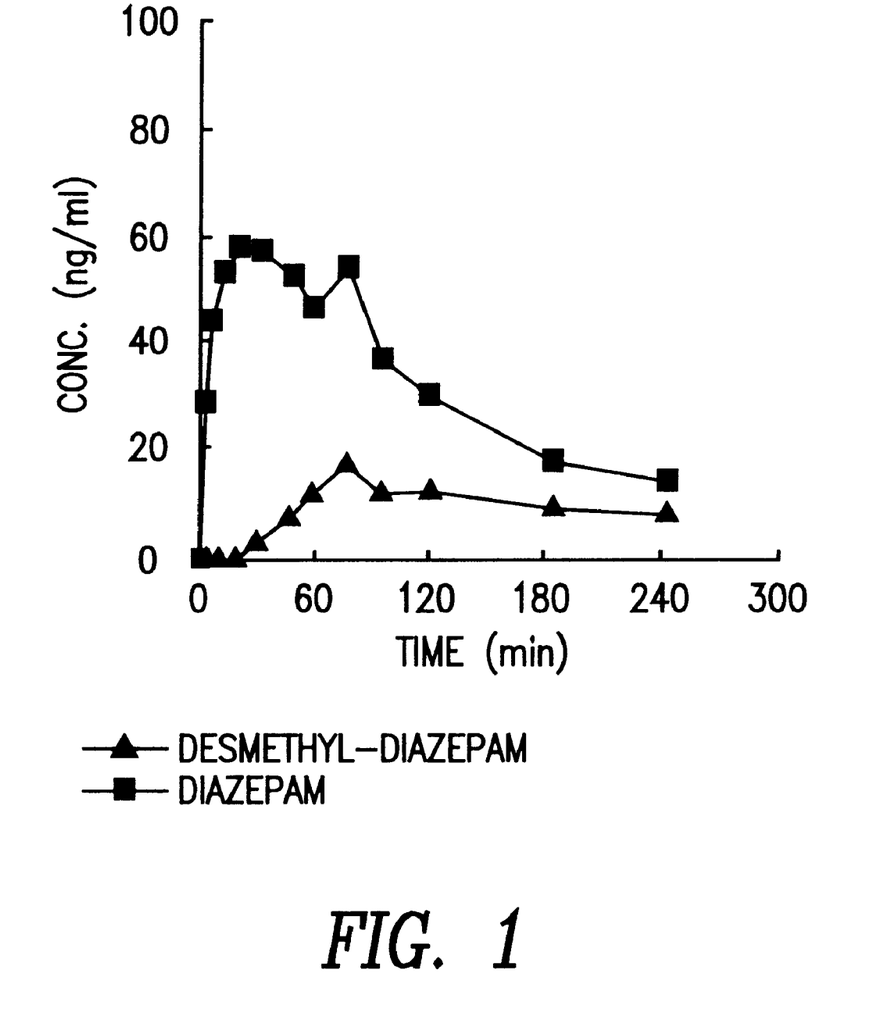
FIG. 1 is a graph showing mean serum concentrations (ng/ml) against time (minutes) after intranasal administration of 2.5 mg diazepam (Formulation C) -▲- Desmethyldiazepam -■- Diazepam.
Figure 2:
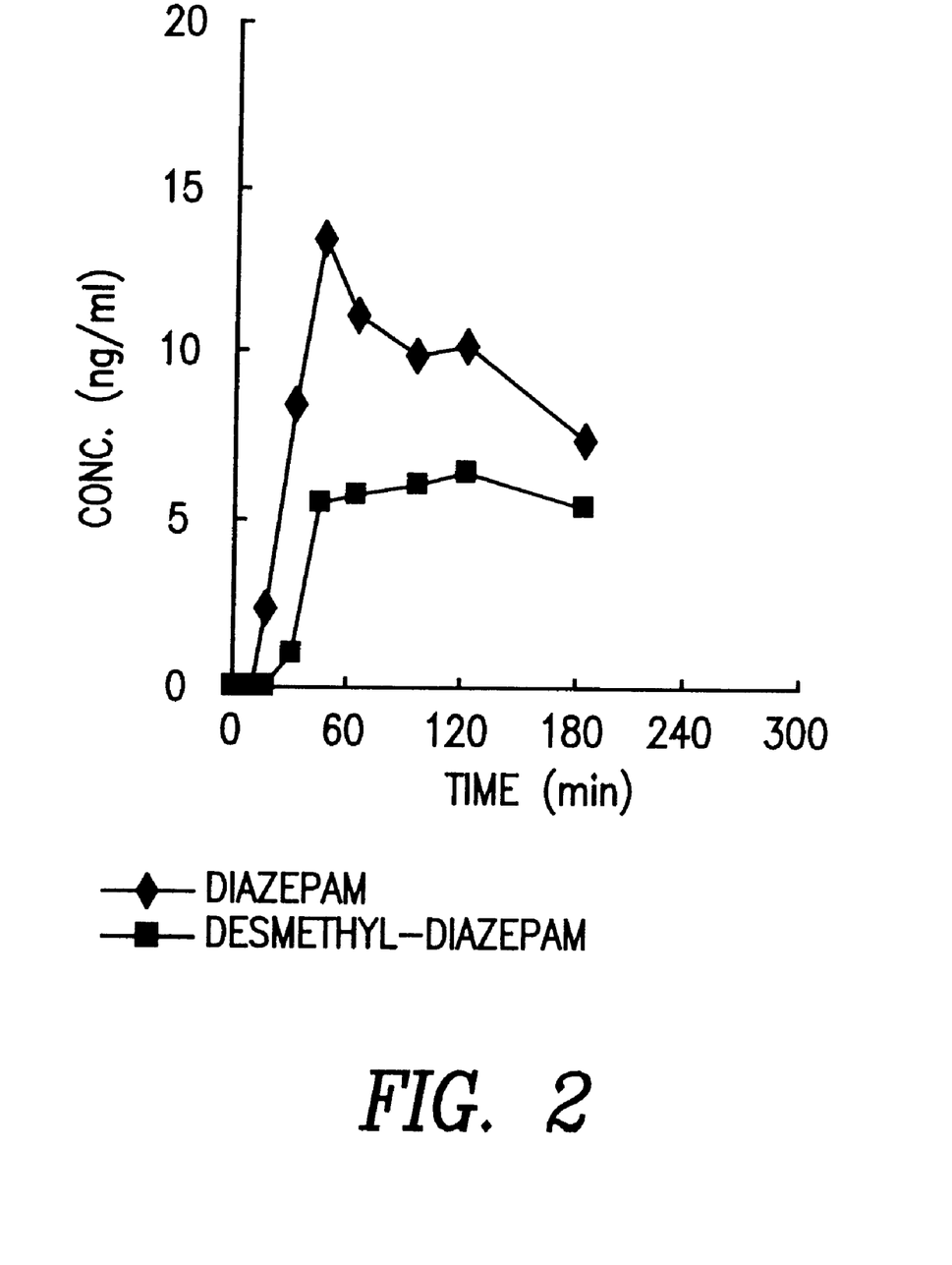
FIG. 2 is a graph showing mean serum concentrations (ng/ml) against time (minutes) after oral administration of 2.0 mg diazepam (Formulation D) -■- Desmethyldiazepam -♦- Diazepam.

FIGS. 1 and 2 illustrate the mean serum concentrations of diazepam and desmethyldiazepam after administration of formulations C and D.

Study 3

This pharmacodynamic study compared Example 8(C) containing 5% of diazepam with Example 19 (E) containing 2.5% of midazolam. The study was using 6 rabbits.

Formulations C and E were given intranasally (i.n.) with a laboratory pipette. Each rabbit was held in a supine position during and one minute after i.n. dosing in one nostril. The rabbits received a volume equivalent to 2.5 mg diazepam or 1.25 mg midazolam, respectively.

After each administration the actual dose received was calculated by subtraction of the weight of the pipette before and after administration. Only doses equivalent to 80% were accepted.

The time to onset of pharmacodynamic response in test 1 was 3.1 minutes (median, n=6) using formulation C containing diazepam and 2.5 minutes (median, n=6) using formulation E containing midazolam.

Example 23

Toxicology

Local Irritancy in Humans:

The investigation was carried out in order to estimate irritation after nasal application of 10 mg of diazepam; 100 mg of the preparation from Example 8 in each nostril.

6 volunteers, 3 male and 3 female participated in the trial.

The investigator inspected both nostrils macroscopically for local irritation at the following times: Immediately after medication, at 30 minutes, and 1, 2, 4, and 6 hours.

In one volunteer the macroscopic inspection showed light blush of both nostrils immediately after medication. None of the six volunteers had local irritation of the nostrils 30 minutes after application, see table 2.

Conclusion

The total results of the trial have shown that preparation of Example 8 does not cause unacceptable irritation of the nostrils.

TABLE 2

Individual local irritation of the nostrils after intranasal administration of 10 mg diazepam, (Example 8)

| Volunteer no | Local irritation | | | | | | | | | | | |
|---|---|---|---|---|---|---|---|---|---|---|---|---|
| | Immediately after medication | | 30 min | | 1 h | | 2 h | | 4 h | | 6 h | |
| | R | L | R | L | R | L | R | L | R | L | R | L |
| 1 | — | — | — | — | — | — | — | — | — | — | — | — |
| 2 | — | — | — | — | — | — | — | — | — | — | — | — |
| 3 | — | — | — | — | — | — | — | — | — | — | — | — |
| 4 | Light blush | Light blush | — | — | — | — | — | — | — | — | — | — |
| 5 | — | — | — | — | — | — | — | — | — | — | — | — |
| 6 | — | — | — | — | — | — | — | — | — | — | — | — |

R: right nostril
L: left nostril

What is claimed is:

1. A composition for the non-topical delivery of an active agent in the form of a non-liposomal emulsion comprising two phases:
   a) a first tocopherol-based phase comprising an active agent which is no more than sparingly soluble in water and which is not a tocopherol; and
   an amount of 20% to 95% w/w based on the total weight of the composition of at least one tocopherol or acetate, linoleate, nicotinate or hemi-succinate derivative thereof sufficient to dissolve the active agent in the tocopherol-based phase;
   b) a second phase comprising an emulsifying agent wherein the emulsifying agent is vitamin E TPGS; wherein said active agent is selected from the group consisting of antibiotics; antivirals; antimycotics; anti-amoebics; non-steroidal anti-inflammatory drugs; anti-allergics; immunosurpressive agents; coronary drugs; analgesics, local anaesthetics; anxiolytics, sedatives and hypnotics; migraine relieving agents; drugs against motion sickness; anti-emetics; disulfiram and vitamin K.

2. A composition as claimed in claim 1 wherein the tocopherol is α-tocopherol or an acetate, linoleate, nicotinate or hemi-succinate derivative thereof.

3. A composition as claimed in claim 1 in a form suitable for transmucosal, peroral, enteral or parenteral application.

4. A composition as claimed in claim 1, in a form of suitable for intranasal, buccal, vaginal or rectal application or for administration via the oral cavity.

5. A composition as claimed in claim 1 wherein the active agent is selected from the group consisting of tetracycline, doxycycline, oxytetracylcline, chloramphenicol, erythromycin, acyclovir, idoxuridine, tromantadine, miconazole, ketoconazole, fluconazole, itraconazole, econazole, griseofulvin, amphotericin B, nystatine, metronidazole, metronidazole benzoate, tinidazole, indomethacin, ibuprofen, piroxicam, diclofenac, disodium cromoglycate, nitroglycerin, isosorbide dinitrate, verapamile, nifedipine, diltiazem, digoxine, morphine, cyclosporins, buprenorphine, lidocaine, diazepam, nitrazepam, flurazepam, estazolam, flunitrazepam, triazolam, alprazolam, midazolam, temazepam lormetazepam, brotizolam, clobazam, clonazepam, lorazepam, oxazepam, busiprone, sumatriptan, ergotamine derivatives, cinnarizine, anti-histamines, ondansetron, tropisetron, granisetrone, metoclopramide, disulfiram, and vitamin K.

6. A composition as claimed in claim 1, wherein the active agent is a coronary drug selected from the group consisting of vasodilators; calcium-antagonists and cardiac-glycosides.

7. A composition as claimed in claim 1, wherein the active agent is a benzodiazepine or an antimycotic.

8. A composition as claimed in claim 1, wherein the active agent is selected from the group consisting of diazepam, midazolam and miconazole.

9. A composition as claimed in claim 1, wherein the amount of the tocopherol or acetate, linoleate, nicotinate or hemi-succinate derivative thereof is from 35 to 80% (w/w).

10. A composition as claimed in claim 1, further comprising at least one additional component selected from the group consisting of solvents, surfactants, stabilizers, bioadhesive polymers, preservatives, odor-masking agents and taste-masking agents.

11. A composition for the non-topical delivery of an active agent in the form of a non-liposomal emulsion comprising two phases:
   a) a first tocopherol-based phase comprising an active agent which is no more than sparingly soluble in water and which is not a tocopherol; and
   an amount of 20% to 95% w/w based on the total weight of the composition of at least one tocopherol or acetate, linoleate, nicotinate or hemi-succinate derivative thereof sufficient to dissolve the active agent in the said tocopherol-based phase;
   b) a second phase comprising an emulsifying agent wherein the emulsifying agent is vitamin E TPGS.

12. A composition as claimed in claim 11 wherein the active agent is selected from the group consisting of antibiotics; antivirals; antimycotics; anti-amoebics; non-steroidal anti-inflammatory drugs; anti-allergics; immunosuppressive agents; coronary drugs; analgesics; local anaesthetics; anxiolytics, sedatives and hypnotics; migraine relieving agents; drugs against motion sickness; anti-emetics; disulfiram and vitamin K.

13. A composition as claimed in claim 12 wherein the active agent is selected from the group consisting of tetracycline, doxycycline, oxytetracycline, chloramphenicol, erythromycin, acyclovir, idoxuridine, tromantadine, miconazole, ketoconazole, fluconazole, itraconazole, econazole, griseofulvin, amphotericin B, nystatine, metronidazole, metronidazole benzoate, tinidazole, indomethacin, ibuprofen, piroxicam, diclofenac, Disodium cromoglycate, nitroglycerin, isosorbide dinitrate, verapamile, nifedipine, diltiazem, digoxine, morphine, cyclosporins, buprenorphine, lidocaine, diazepam, nitrazepam, flurazepam, estazolam, flunitrazepam, triazolam, alprazolam, midazolam, temazepam, lormetazepam, brotizolam, clobazam, clonazepam, lorazepam, oxazepam, busiprone, sumatriptan, ergotamine derivatives, cinnarizine, anti-histamines, ondansetron, tropisetron, granisetrone, metoclopramide, disulfiram, and vitamin K.

14. A composition as claimed in claim 11 wherein the tocopherol is α-tocopherol or an acetate, linoleate, nicotinate or hemi-succinate derivative thereof.

15. A composition as claimed in claim 11 in a form suitable for transmucosal, peroral, enteral or parenteral application.

16. A composition as claimed in claim 11, in a form suitable for intranasal, buccal, vaginal or rectal application or for administration via the oral cavity.

17. A composition as claimed in claim 11, wherein the active agent is a coronary drug selected from the group consisting of vasodilators; calcium-antagonists and cardiac-glycosides.

18. A composition as claimed in claim 11, wherein the active agent is a benzodiazepine or an antimycotic.

19. A composition as claimed in claim 11, wherein the active agent is selected from the group consisting of diazepam, midazolam and miconazole.

20. A composition as claimed in claim 11, wherein the amount of the tocopherol or acetate, linoleate, nicotinate or hemi-succinate derivative thereof is from 35 to 80% (w/w).

21. A composition as claimed in claim 11, further comprising at least one additional component selected from the group consisting of solvents, surfactants, stabilizers, bioadhesive polymers, preservatives, odor-masking agents and taste-masking agents.

22. A composition for the parenteral delivery of an active agent in the form of a non-liposomal emulsion comprising two phases:
   a) a first tocopherol-based phase comprising an active agent which is no more than sparingly soluble in water and which is not a tocopherol; and
   an amount of 20% to 95% w/w based on the total weight of the composition of at least one tocopherol or acetate, linoleate, nicotinate or hemi-succinate derivative thereof sufficient to dissolve the active agent in the tocopherol-based phase;
   b) a second phase comprising an emulsifying agent wherein the emulsifying agent is vitamin E TPGS.

23. A composition as claimed in claim 22 wherein the active agent is selected from the group consisting of antibiotics; antivirals; antimycotics, anti-amoebics; non-steroidal anti-inflammatory drugs; anti-allergics; immunosuppressive agents; coronary drugs; analgesics, local anaesthetics; anxiolytics, sedative and hypnotics; migraine relieving agents; drugs against motion sickness; antiemetics; disulfiram and vitamin K.

24. A composition as claimed in claim 23 wherein the active agent is selected from the group consisting of tetracycline, doxycycline, oxytetracycline, chloramphenicol, erythromycin, acyclovir, idoxuridine, tromantadine, miconazole, ketoconazole, fluconazole, itraconazole, econazole, griseofulvin, amphotericin B, nystatine, metronidazole, metronidazole benzoate, tinidazole, indomethacin, ibuprofen, piroxicam, diclofenac, Disodium cromoglycate, nitroglycerin, isosorbide dinitrate, verapamile, nifedipine, diltiazem, digoxine, morphine, cyclosporins, buprenorphine, lidocaine, diazepam, nitrazepam, flurazepam, estazolam, flunitrazepam, triazolam, alprazolam, midazolam, temazepam, lormetazepam, brotizolam, clobazam, clonazepam, lorazepam, oxazepam, busiprone, sumatriptan, ergotamine derivatives, cinnarizine, anti-histamines, ondansetron, tropisetron, granisetrone, metoclopramide, disulfiram, and vitamin K.

25. A composition as claimed in claim 22 wherein the tocopherol is α-tocopherol or an acetate, linoleate, nicotinate or hemi-succinate derivative thereof.

26. A composition as claimed in claim 22, wherein the active agent is a coronary drug selected from the group consisting of vasodilators; calcium-antagonists and cardiac-glycosides.

27. A composition as claimed in claim 22, wherein the active agent is a benzodiazepine or an antimycotic.

28. A composition as claimed in claim 22, wherein the active agent is selected from the group consisting of diazepam, midazolam and miconazole.

29. A composition as claimed in claim 22, wherein the amount of tocopherol or acetate, linoleate, nicotinate or hemi-succinate derivative thereof is from 35 to 80% (w/w).

30. A composition as claimed in claim 22, further comprising at least one additional component selected from the group consisting of solvents, surfactants, stabilizers, bioadhesive polymers, preservatives, odor-masking agents and taste-masking agents.

* * * * *